(12) United States Patent  (10) Patent No.: US 9,144,406 B2
Dennerlein  (45) Date of Patent: Sep. 29, 2015

(54) CONFIGURATION AND METHOD FOR TOMOSYNTHETIC FLUOROSCOPY

(71) Applicant: SIEMENS AKTIENGESELLSCHAFT, Munich (DE)

(72) Inventor: Frank Dennerlein, Forchheim (DE)

(73) Assignee: Siemens Aktiengesellschaft, Munich (DE)

( * ) Notice: Subject to any disclaimer, the term of this patent is extended or adjusted under 35 U.S.C. 154(b) by 164 days.

(21) Appl. No.: 14/043,108

(22) Filed: Oct. 1, 2013

(65) Prior Publication Data

US 2014/0093032 A1  Apr. 3, 2014

(30) Foreign Application Priority Data

Oct. 1, 2012 (DE) .......................... 10 2012 217 966

(51) Int. Cl.
*A61B 6/02* (2006.01)
*A61B 6/00* (2006.01)
*A61B 6/06* (2006.01)

(52) U.S. Cl.
CPC .............. *A61B 6/025* (2013.01); *A61B 6/4007* (2013.01); *A61B 6/487* (2013.01); *A61B 6/06* (2013.01)

(58) Field of Classification Search
CPC ........ A61B 6/032; A61B 6/035; A61B 6/025; A61B 6/02; A61B 6/4429; A61B 6/022; A61B 6/4464; A61B 6/447; H04N 5/321
USPC ................ 378/4, 21, 23, 25, 27, 42, 196, 197
See application file for complete search history.

(56) References Cited

U.S. PATENT DOCUMENTS

| 3,091,692 | A * | 5/1963 | Verse ............................... 378/22 |
| 7,050,535 | B2 | 5/2006 | Georgeson et al. |
| 7,527,429 | B2 | 5/2009 | Francke |
| 7,936,858 | B2 | 5/2011 | Hashemi et al. |
| 8,094,773 | B2 | 1/2012 | Boese et al. |
| 8,873,716 | B2 | 10/2014 | Ren et al. |
| 2005/0199059 | A1 | 9/2005 | Danz et al. |
| 2009/0092225 | A1 | 4/2009 | Boese et al. |
| 2009/0323893 | A1 | 12/2009 | Hanke et al. |
| 2011/0268341 | A1 | 11/2011 | Boese et al. |

FOREIGN PATENT DOCUMENTS

| CN | 1647762 A | 8/2005 |
| CN | 101808582 A | 8/2010 |
| CN | 102176866 A | 9/2011 |
| DE | 3243449 A1 | 5/1984 |
| DE | 19743577 A1 | 4/1999 |
| DE | 102009043421 A1 | 4/2011 |
| DE | 102010028438 A1 | 11/2011 |
| DE | 102010028446 A1 | 11/2011 |

* cited by examiner

*Primary Examiner* — Jurie Yun
(74) *Attorney, Agent, or Firm* — Laurence A. Greenberg; Werner H. Stemer; Ralph E. Locher

(57) ABSTRACT

A configuration and an associated operating method for tomosynthetic fluoroscopy utilize an x-ray emitter and with an x-ray detector. The configuration further contains a mounting device, which is rotatably mounted about a rotational axis and about which the x-ray emitter is arranged such that the optical axis of the x-ray emitter is directed to the x-ray detector and that, in the case of a rotation of the mounting device, the focus of the x-ray emitter describes a circular path. An advantage offered by the invention lies in ensuring robust tomosynthetic fluoroscopy.

9 Claims, 2 Drawing Sheets

CONFIGURATION AND METHOD FOR TOMOSYNTHETIC FLUOROSCOPY

CROSS-REFERENCE TO RELATED APPLICATION

This application claims the priority, under 35 U.S.C. §119, of German application DE 10 2012 217 966.6, filed Oct. 1, 2012; the prior application is herewith incorporated by reference in its entirety.

BACKGROUND OF THE INVENTION

Field of the Invention

The invention relates to a configuration and a method for tomosynthetic fluoroscopy, with an x-ray emitter, the focus of which carries out a controlled movement.

These days, fluoroscopy instruments are utilized in many fields of application, for example for gastrointestinal examinations. Fluoroscopy instruments are used to record sequences, using x-ray radiation, of two-dimensional projection images of a patient with a high frame rate in order to display a dynamic process in the patient. By way of example, such a dynamic process can be the propagation of contrast agent or the movement of medical instruments in the case of needle or catheter interventions.

These days, fluoroscopy imaging merely supplies two-dimensional image information. The information relating to at which depth, i.e. at what distance to the x-ray source, an imaged structure is situated is not captured by projection images. Since there is no separation of depth information, the medically relevant structures can be superposed and covered by information relating to other anatomical structures (e.g. bones). Furthermore, the two-dimensional image does not allow precise spatial detection of the position of an instrument in relation to the patient.

It is known to apply a multi-beam x-ray source with carbon nanotubes (CNT), the individual sources of which can be switched on and off electronically, to a beam therapy system instead of or in addition to the x-ray source. As a result, it is possible to record projection images very quickly from different angles distributed about the main viewing direction, from which projection images it is subsequently possible to reconstruct a tomosynthesis volume. As a result of the tomosynthesis data record, a partial depth resolution is possible, i.e. a user of the instrument can mask structures from depth layers that are not of interest. A corresponding implementation in angiography instruments is proposed in published, non-prosecuted German patent application DE 10 2009 043 421 A1, corresponding to U.S. Pat. No. 8,094,773. A use for fluoroscopy operation would be possible if the application of the CNT multi-x-ray source is robust and reliable.

U.S. patent disclosure No. 2007/0223650 A1 discloses an x-ray emitter which is arranged rotatable about a vertical axis.

U.S. patent disclosure No. 2006/0056585 A1 likewise discloses an x-ray emitter which is arranged rotatable about a vertical axis.

Moreover, published, non-prosecuted German patent application DE 10 210 028 438 A1 discloses an x-ray emitter which is arranged rotatable about a vertical axis.

SUMMARY OF THE INVENTION

It is accordingly an object of the invention to provide a configuration and an associated method for tomosynthetic fluoroscopy that overcome the above-mentioned disadvantages of the prior art devices and methods of this general type, which ensure robust and stable operation.

The core of the invention consists of mechanically augmenting an x-ray emitter arrangement provided for a fluoroscopy application in such a way that the x-ray emitter can be rotated quickly, wherein the focus of the x-ray emitter describes a circular path, the radius of which can be modified quickly and easily. With the proposed arrangement, it is possible to acquire projection data for circular tomosynthesis while the patient is irradiated such that tomographic fluoroscopy imaging is possible. Such an operating state significantly increases the functionality of a fluoroscopy instrument, since, compared to 2D projection imaging, it now becomes possible to discriminate depth information. By way of example, it is now possible as a result of this to mask structures in the foreground or background of the relevant body region during visualization.

The invention claims an arrangement for tomosynthetic fluoroscopy, with an x-ray emitter and with an x-ray detector, wherein an x-ray emitter is arranged on a mounting device rotatably mounted about a rotational axis such that the optical axis of the x-ray emitter is directed to the x-ray detector and that, in the case of a rotation of the mounting device, the focus of the x-ray emitter describes a circular path. In so doing, the x-ray emitter is displaceably arranged in the direction of the rotational axis. An advantage offered by the invention is that the radius of the circular path of the focus can easily be modified.

Advantageously, the configuration can also contain a counterbalance, which is arranged symmetrically with respect to the rotational axis, opposite to the x-ray emitter on the mounting device. As result, imbalance during a rotation of the mounting device is avoided.

Moreover, the counterbalance can approximately have the same mass as the x-ray emitter.

In a development, the counterbalance can be displaceably arranged in the direction of the rotational axis, as a result of which the distance of the counterbalance from the rotational axis can be set corresponding to the distance of the x-ray emitter from the rotational axis.

The mounting device can advantageously have the shape of a disk, as a result of which no imbalance occurs during a rotation.

In a further embodiment, the arrangement can contain an x-ray collimator, which is arranged in front of the x-ray emitter in the direction of the optical axis such that it rotates together with the x-ray emitter and emits a tilted x-ray beam cone in the direction of the rotational axis.

The mounting device can advantageously have a displaceable and/or tiltable configuration.

The invention also claims an operating method for tomosynthetic fluoroscopy, wherein, in the case of a rotation of a mounting device rotatably mounted about a rotational axis, the focus of an x-ray emitter connected to the mounting device describes a circular path and wherein the x-ray emitter is displaced in the direction of the rotational axis.

The invention also claims a fluoroscopy instrument with an arrangement according to the invention.

Other features which are considered as characteristic for the invention are set forth in the appended claims.

Although the invention is illustrated and described herein as embodied in a configuration and a method for tomosynthetic fluoroscopy, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DETAILED DESCRIPTION OF THE INVENTION

Figure 1:
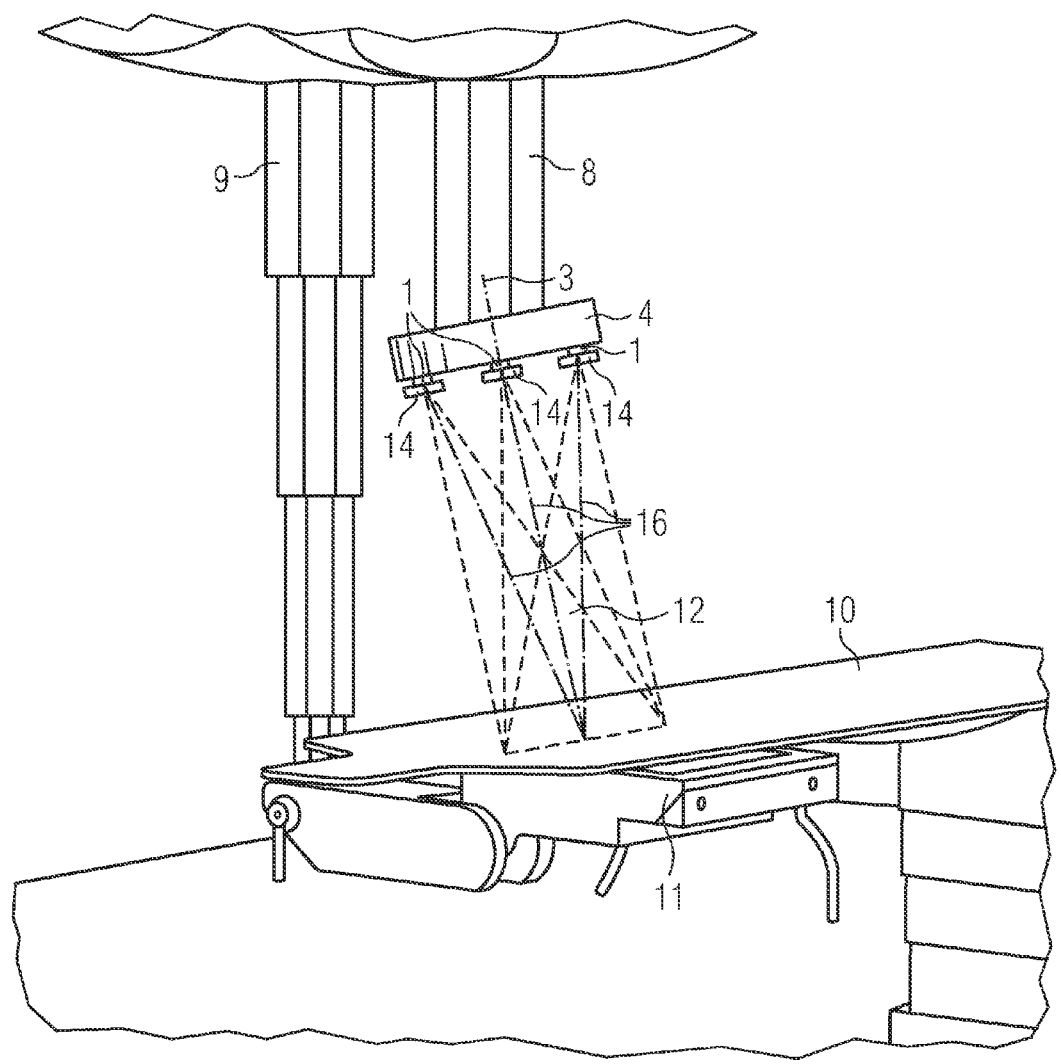
FIG. 1 is a diagrammatic, perspective view of a fluoroscopy instrument.

Referring now to the figures of the drawings in detail and first, particularly to FIG. 1 thereof, there is shown in a perspective view, a fluoroscopy instrument with an arrangement according to the invention. A disk-shaped mounting device 4 is attached to a ceiling mount 8. A patient couch 10 is attached under the mounting device 4 by a telescopic arm 9. The mounting device 4 can be rotated about a rotational axis 3 and can also be tilted from the perpendicular. An x-ray emitter 1 is arranged on an underside of the mounting device 4 in such a way that it rotates with the mounting device 4. In the process, the focus (not illustrated) of the x-ray emitter 1 describes a circular path. The x-ray emitter 1 and x-ray radiation 12 emitted thereby are depicted in three different positions which are rotated with respect to one another.

The x-ray radiation 12 impinges on an x-ray detector 11 situated under the patient couch 10, which x-ray detector 11 lies in a direction of an optical axis 16 of the x-ray emitter 1. The emitted conical x-ray radiation 12 can be slightly tilted in the direction of the rotational axis 3 with the aid of an x-ray collimator 14, which rotates with the x-ray tube 1. This, and the distance from the rotational axis 3, which is selected for the current distance between the mounting device 4 and the x-ray detector 11, ensures that the x-ray radiation 12 in each case impinges on the same area in the plane of the x-ray detector 11, independently of the current rotational position of the x-ray emitter 1.

Two methods are possible for operating the arrangement according to the invention: firstly, 2D projection imaging and secondly tomosynthetic fluoroscopy. 2D projection imaging is similar to conventional fluoroscopy. The x-ray emitter 1 is locked within the mounting device 4 and positioned appropriately with respect to the patient. The fluoroscopy recordings that are created are sequences of two-dimensional projection images at a high image frequency.

In the case of tomosynthetic fluoroscopy, the x-ray emitter 1 is rotated during the image acquisition. By way of example, the rotation takes place at one rotation per second and, in so doing, the x-ray emitter 1 is operated in a pulsed mode. The acquired image data can now be used for volumetric imaging by circular tomosynthesis with a relatively high frame rate. By way of example, a complete update of the tomosynthesis volume can occur with a frequency of 1 Hz. Partial updates can occur with a higher image frequency, as described in the published, non-prosecuted German patent application DE 10 2009 043 421 A1 cited above. The reconstructed tomosynthesis volumes are then visualized either slice-by-slice or as a rendering of the whole volume or a partial volume, in which the interfering patient regions can be masked using clipping planes. By way of example, a removal of spinal or thoracic bones in the visualization is possible.

Figure 2:
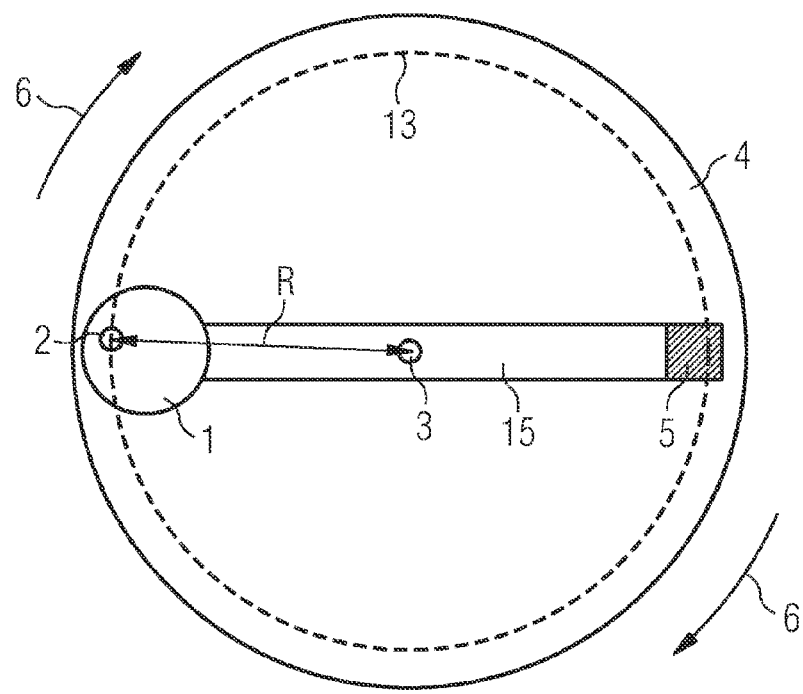
FIG. 2 is a top view of a mounting device according to the invention.

FIG. 2 shows a top view of a detail according to the invention from FIG. 1. What can be seen is the disk-shaped mounting device 4, which can rotate about the rotational axis 3 in a rotational direction 6. The x-ray emitter 1 is arranged at one end of a guide groove 15 provided in the mounting device 4. When the mounting device 4 rotates, a focus 2 of the x-ray emitter 1 describes a circular path 13 about the rotational axis 3. At the other end of the guide groove 15, a counterbalance 5 has been applied in order to avoid imbalance during the rotation.

The tomosynthesis image quality that can be achieved is also determined by a distance R between the focus 2 and the rotational axis 3, which prescribes the maximum tomosynthesis angle. Thus, for a further embodiment of the arrangement according to the invention, it is proposed to modify the radius R by translation of the x-ray emitter 1. In so doing, both the x-ray emitter 1 and the counterbalance 5 are displaced in the guide groove 15 in the direction of the rotational axis 3.

Figure 3:
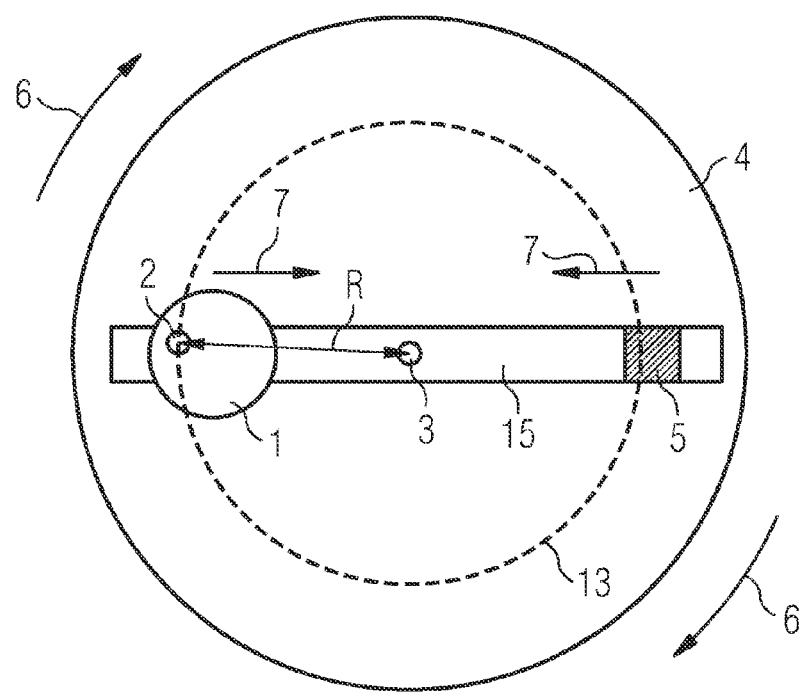
FIG. 3 is a top view of a further mounting device according to the invention.

Such a shifted position is depicted in FIG. 3. The x-ray emitter 1 and the counterbalance 5 are displaced from an end position in the displacement direction 7, as a result of which the radius R of the focus movement is reduced. Otherwise, the illustration in FIG. 3 corresponds to that of FIG. 2.

The proposed configuration and the associated method moreover allow further applications. In the case of real-time stereo fluoroscopy, stereo image pairs can be obtained by image acquisition at in each case two fixedly defined positions along the rotational movement of the x-ray emitter 1. A spatial real-time localization of intervention instruments during a biopsy or a catheter examination is likewise possible. In the case of dynamic perfusion imaging, there is a reconstruction of time series by tomosynthesis for following the dynamics of a contrast agent injection for establishing functional tissue parameters.

The invention claimed is:

1. A configuration for tomosynthetic fluoroscopy, comprising:
   an x-ray emitter defining an optical axis and a focus;
   an x-ray detector;
   a mounting device rotatably mounted about a rotational axis and about which said x-ray emitter is disposed such that said optical axis of said x-ray emitter is directed to said x-ray detector and that, in a case of a rotation of said mounting device, said focus of said x-ray emitter describes a circular path; and
   said x-ray emitter being displaceably disposed in a direction of the rotational axis.

2. The configuration according to claim 1, further comprising a counterbalance, which is disposed symmetrically with respect to the rotational axis, opposite to said x-ray emitter on said mounting device.

3. The configuration according to claim 2, wherein said counterbalance has a same mass as said x-ray emitter.

4. The configuration according to claim 2, wherein said counterbalance is displaceably disposed in the direction of the rotational axis.

5. The configuration according to claim 1, wherein said mounting device has a shape of a disk.

6. The configuration according to claim 1, further comprising an x-ray collimator disposed in front of said x-ray emitter in a direction of the optical axis such that said x-ray collimator rotates together with said x-ray emitter.

7. The configuration according to claim 1, wherein said mounting device is at least one of displaceable or tiltable.

8. A method for operating a configuration for tomosynthetic fluoroscopy, which comprises the step of:
rotating a mounting device rotatably mounted about a rotational axis, a focus of an x-ray emitter connected to the mounting device carrying out a circular path; and
displacing the x-ray emitter in a direction of the rotational axis.

9. A fluoroscopy instrument, comprising:
an x-ray emitter defining an optical axis and a focus;
an x-ray detector;
a mounting device rotatably mounted about a rotational axis and about which said x-ray emitter is disposed such that said optical axis of said x-ray emitter is directed to said x-ray detector and that, in a case of a rotation of said mounting device, said focus of said x-ray emitter describes a circular path; and
said x-ray emitter being displaceably disposed in a direction of the rotational axis.

\* \* \* \* \*